US012599437B2

(12) United States Patent
Dickhans et al.

(10) Patent No.: US 12,599,437 B2
(45) Date of Patent: Apr. 14, 2026

(54) PRE-PROCEDURE PLANNING, INTRA-PROCEDURE GUIDANCE FOR BIOPSY, AND ABLATION OF TUMORS WITH AND WITHOUT CONE-BEAM COMPUTED TOMOGRAPHY OR FLUOROSCOPIC IMAGING

(71) Applicant: Covidien LP, Mansfield, MA (US)

(72) Inventors: William J. Dickhans, Longmont, CO (US); Oren P. Weingarten, Hod-Hasharon (IL); Evgeni Kopel, Barkan (IL); Avital Zik, Tel Aviv (IL); Ariel Birenbaum, Raanana (IL)

(73) Assignee: Covidien LP, Mansfield, MA (US)

( * ) Notice: Subject to any disclaimer, the term of this patent is extended or adjusted under 35 U.S.C. 154(b) by 701 days.

(21) Appl. No.: 17/955,224

(22) Filed: Sep. 28, 2022

(65) Prior Publication Data

US 2023/0130294 A1     Apr. 27, 2023

Related U.S. Application Data

(60) Provisional application No. 63/270,424, filed on Oct. 21, 2021.

(51) Int. Cl.
*A61B 34/20* (2016.01)
*A61B 18/00* (2006.01)
(Continued)

(52) U.S. Cl.
CPC .............. *A61B 34/20* (2016.02); *A61B 34/10* (2016.02); *A61B 34/25* (2016.02);
(Continued)

(58) Field of Classification Search
CPC ......... A61B 34/10; A61B 34/20; A61B 34/25; A61B 34/30; A61B 90/37;
(Continued)

(56) References Cited

U.S. PATENT DOCUMENTS

2018/0055582 A1* 3/2018 Krimsky ................ G16H 50/50

FOREIGN PATENT DOCUMENTS

EP     3372185 A1     9/2018
EP     3811887 A1     4/2021
(Continued)

OTHER PUBLICATIONS

Mayo Clinic Staff, Reducing Radiation Exposure One Image at a Time (Year: 2015).*

(Continued)

*Primary Examiner* — Nancy Bitar
(74) *Attorney, Agent, or Firm* — Weber Roselli & Cannon LLP

(57) ABSTRACT

A system and method for navigation of a luminal network including receiving a computed tomography (CT) image data set, generating a three-dimensional (3D) model, displaying the 3D model in a user-interface on a display operatively connected to the computing device, and receiving an indication of a location of a tumor in the CT image data set. The system and method further including displaying the location of the tumor in the 3D model, receiving an indication of a margin around the tumor to achieve a desired therapy, generating a pathway to the tumor for navigation of a catheter, receiving a location of a sensor associated with a navigation catheter and registering the CT image data set with a luminal network of a patient, displaying the location of the sensor within the 3D model that substantially corresponds to the location of the sensor within the luminal network of the patient.

20 Claims, 10 Drawing Sheets

(51) Int. Cl.

| | |
|---|---|
| *A61B 34/00* | (2016.01) |
| *A61B 34/10* | (2016.01) |
| *A61B 34/30* | (2016.01) |
| *A61B 90/00* | (2016.01) |

(52) U.S. Cl.

CPC ............... *A61B 2018/00541* (2013.01); *A61B 2018/00577* (2013.01); *A61B 2034/107* (2016.02); *A61B 2034/2046* (2016.02); *A61B 2034/2051* (2016.02); *A61B 2034/2061* (2016.02); *A61B 2034/2072* (2016.02); *A61B 2034/301* (2016.02); *A61B 90/37* (2016.02); *A61B 2090/376* (2016.02); *A61B 2090/3764* (2016.02)

(58) Field of Classification Search

CPC .......... A61B 2018/00541; A61B 2018/00577; A61B 2034/105; A61B 2034/107; A61B 2034/2046; A61B 2034/2051; A61B 2034/2061; A61B 2034/2072; A61B 2034/301; A61B 2090/376; A61B 2090/3764

See application file for complete search history.

(56) References Cited

FOREIGN PATENT DOCUMENTS

| WO | 2016069324 A1 | 5/2016 | |
| WO | WO-2019231891 A1 * | 12/2019 | ............ A61B 34/30 |
| WO | 2021105785 A1 | 6/2021 | |

OTHER PUBLICATIONS

Partial European Search Report issued in European Patent Application No. 22203063.7 dated Mar. 20, 2023.

* cited by examiner

502

500

504

506

PRE-PROCEDURE PLANNING, INTRA-PROCEDURE GUIDANCE FOR BIOPSY, AND ABLATION OF TUMORS WITH AND WITHOUT CONE-BEAM COMPUTED TOMOGRAPHY OR FLUOROSCOPIC IMAGING

CROSS-REFERENCE TO RELATED APPLICATIONS

This application claims benefit of and priority to U.S. Provisional Application No. 63/270,424 filed Oct. 21, 2021, the disclosure of which is hereby incorporated by reference in its entirety.

FIELD

The disclosed technology is generally related to intraluminal navigation and therapy systems and methods.

BACKGROUND

Current technology includes catheter systems that enable navigation of a catheter tip through a tortuous lumen of the body to a target. This technology involves the real-time movement of a catheter using medical images, e.g., computerized tomography (CT) images, of a targeted area of the body. Navigation may be presented as a recommended path based on the structure of the anatomy (e.g., an airway bronchiole structure) shown in the medical images. During navigation, however, the catheter systems may be unable to cause the distal portion of the catheter to reach all positions with an acceptable alignment to target.

In addition, though pre-procedure imaging can provide high quality images for planning of a pathway to targets within, for example, the airways of a patient, a divergence between the relative positions of structures within the patient during the imaging and how they are positioned during a subsequent procedure (e.g., CT-Body divergence) can result in errors that make accurate placement of biopsy and ablation catheters within a target (e.g., a tumor or lesion) and centered within that target very difficult. Accordingly, improvements to existing navigation systems.

SUMMARY

One aspect of the disclosure is directed to a system for planning and navigation of a luminal network a computing device including a memory and a processor, the memory storing one or more applications that when executed by the processor execute the steps of: receiving a computed tomography (CT) image data set; generating a three-dimensional (3D) model: displaying the 3D model in a user-interface on a display operatively connected to the computing device; receiving an indication of a location of a tumor in the CT image data set; displaying the location of the tumor in the 3D model; receiving an indication of a margin around the tumor to achieve a desired therapy; generating a pathway plan to the tumor for navigation of a catheter; receiving a location of a sensor associated with a navigation catheter and registering the CT image data set with a luminal network of a patient; displaying the location of the sensor within the 3D model that substantially corresponds to the location of the sensor within the luminal network of the patient; displaying, following the pathway plan, the navigation of the navigation catheter to tumor; receiving an intraprocedural image data set; updating a relative position of the tumor and the navigation catheter in the 3D model based on the intraprocedural image data set; displaying in the 3D model the navigation catheter advanced into the tumor; receiving a second intraprocedural image data set depicting the navigation catheter with respect to the tumor; receiving an indication that an ablation catheter has been advanced through the navigation catheter; and initiating ablation of the tumor. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the margin is automatically generated. The tumor is located beyond an airway wall. The system further including displaying the access point on the user interface at a location in the 3D model. The system further including receiving an indication that the ablation catheter is properly placed in the tumor. The intraprocedural image data set depicts a progression of the ablation. The first, second, and third intraprocedural image data sets are fluoroscopic images or cone beam CT images. The pathway plan is registered to the second or third intraprocedural image data sets. The system further including displaying at least a portion of the pathway plan, an access point, the tumor, or the margin on the second or third intraprocedural image data set. The system further including displaying an ablation zone on the third intraprocedural image data set. The system further including receiving an instruction to adjust the ablation zone before initiating the ablation. The critical structures are overlaid on the first or second intraprocedural image data set. Either the first or the second intraprocedural image data sets are acquired at a decreased radiation dose. During the first or second intraprocedural image data set acquisition certain frames of the image data set are skipped to reduce a radiation dose of the imaging. The system further including receiving an indication of critical structures or key structures and a minimum distance to maintain from the critical structures or key structures. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A second aspect of the disclosure is directed to a system for planning and navigation of a luminal network. The system also includes a navigation catheter configured for insertion into a luminal network of a patient. The system also includes a sensor associated with the catheter for detecting a position of the navigation catheter within the luminal network of the patient; a computing device including a memory and a processor, the memory storing one or more applications that when executed by a processor: displays a 3D model of the luminal network of a patient, the 3D model including airways and blood vessels of the luminal network, a pathway through the luminal network, a tumor including a margin, and where the tumor is located beyond an airway wall an access point, and a position of the catheter within the luminal network of the patient based on the detected position of the sensor; receives intraprocedural images; overlays at least a portion of the 3D model onto the intraprocedural images. The system also includes an ablation catheter configured for receipt into the navigation catheter for treatment of the tumor. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the intraprocedural images are displayed on a user interface as the ablation catheter is inserted into the tumor. Prior to insertion of the ablation catheter an ablation zone, determined prior to a therapy procedure, is displayed on the intraprocedural images and the ablation zone may be adjusted prior to initiation of the ablation. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method including receiving a computed tomography (CT) image data set; generating a three-dimensional (3D) model: displaying the 3D model in a user-interface on a display operatively connected to a computing device; receiving an indication of a location of a tumor in the CT image data set; displaying the location of the tumor in the 3D model; receiving an indication of a margin around the tumor to achieve a desired therapy; generating a pathway plan to the tumor for navigation of a catheter; receiving a location of a sensor associated with a navigation catheter and registering the CT image data set with a luminal network of a patient; displaying the location of the sensor within the 3D model that substantially corresponds to the location of the sensor within the luminal network of the patient; displaying, following the pathway plan, the navigation of the navigation catheter to tumor; receiving an intraprocedural image data set; updating a relative position of the tumor and the navigation catheter in the 3D model based on the intraprocedural image data set; displaying in the 3D model the navigation catheter advanced into the tumor; receiving a second intraprocedural image data set depicting the navigation catheter with respect to the tumor; receiving an indication that an ablation catheter has been advanced through the navigation catheter; and initiating ablation of the tumor. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including determining a location of an access point on a wall of the luminal network to access the tumor, where the tumor is located beyond an airway wall. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

DETAILED DESCRIPTION

Figure 1:
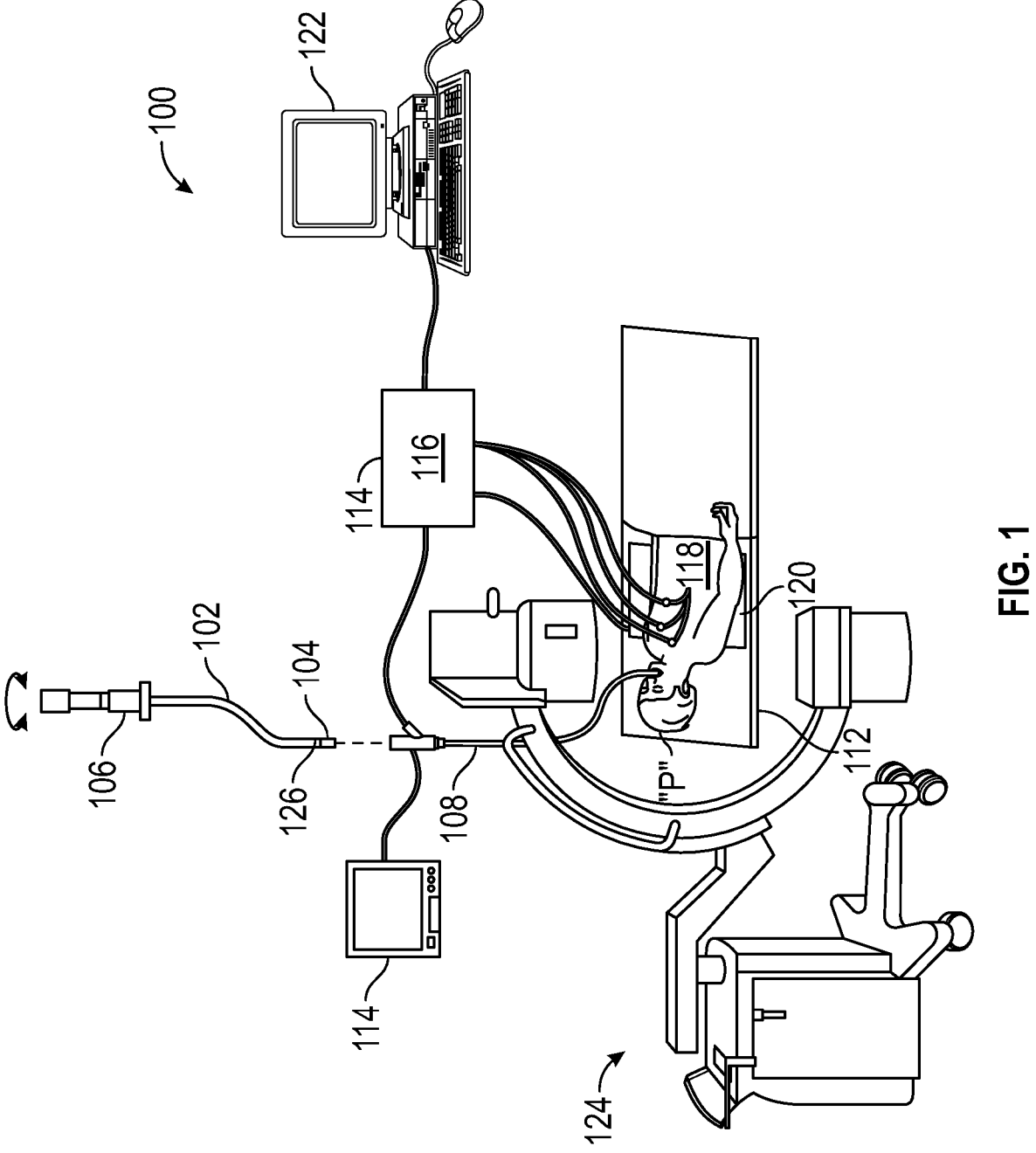
FIG. 1 is a perspective view of an electromagnetic navigation and imaging system in accordance with this disclosure.

FIG. 1 is a perspective view of an exemplary system for facilitating navigation of a medical device, e.g., a catheter, to a soft-tissue target via airways of the lungs. System 100 may be further configured to construct fluoroscopic based 3D volumetric data of the target area from 2D fluoroscopic images to confirm navigation to a desired location. Additionally or alternatively, the imaging device of system 100 may be configured for cone-beam computed tomography (CBCT) imaging as described in greater detail below. System 100 may be further configured to facilitate approach of a medical device to the target area by using Electromagnetic Navigation (EMN) and for determining the location of a medical device with respect to the target. One such EMN system is the ILLUMISITE system currently sold by Medtronic PLC, though other systems for intraluminal navigation are considered within the scope of the disclosure, as noted above.

One aspect of the system 100 is a software component for reviewing of computed tomography (CT) image scan data that has been acquired separately from system 100. The review of the CT image data allows a user to identify one or more targets, plan a pathway to an identified target (planning phase), navigate a catheter 102 to the target (navigation phase) using a user interface on computing device 122, and confirming placement of a sensor 104 relative to the target. The target may be tissue of interest identified by review of the CT image data during the planning phase. Following navigation, a medical device, such as a biopsy tool, an access tool, or a therapy tool (e.g., flexible microwave ablation catheter), may be inserted into catheter 102 to obtain a tissue, enable access to a target site, or apply therapy to a target site.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110 (a second catheter), including a sensor 104 is inserted into catheter 102 and locked into position such that sensor 104 extends a desired distance beyond the distal tip of catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 118 and a transmitter mat 120. The transmitter mat 120 may include a plurality of incorporated markers. System 100 further includes a computing device 122 for on which software and/or hardware are used to facilitate identification of a target, planning a pathway to the target, navigating a medical device to the target, and/or confirmation and/or determination of placement of catheter 102, or a suitable device therethrough, relative to the target.

As noted above, an imaging device 124 capable of acquiring fluoroscopic images or video or CBCT images of the patient P is also included in this particular aspect of system 100. The images, sequence of images, or video captured by imaging device 124 may be stored within imaging device 124 or transmitted to computing device 122 for storage, processing, and display. Additionally, imaging device 124 may move relative to the patient P so that images may be acquired from different angles or perspectives relative to patient P to create a sequence of images, such as a fluoroscopic video. The pose of imaging device 124 relative to patient P and while capturing the images may be estimated via markers incorporated with the transmitter mat 120, in the operating table 112, or a pad (not shown) placed between the patient and the operating table 112. The markers are positioned under patient P, between patient P and operating table 112 and between patient P and a radiation source or a sensing unit of imaging device 124. The markers may have a symmetrical spacing or may have an asymmetrical spacing, a repeating pattern, or no pattern at all. Imaging device 124 may include a single imaging device or more than one imaging device. When a CBCT device is employed, the captured images can be employed to confirm the location of a tool within the patient, update CT-based 3D modeling, or replaced pre-procedural 3D modeling with intra-procedural modeling of the patient's airways and the position of the catheter 102 within the patient.

Computing device 122 may be any suitable computing device including a processor and storage medium, wherein the processor is capable of executing instructions stored on the storage medium. Computing device 122 may further include a database configured to store patient data, CT data sets including CT images, CBCT images and data sets, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the navigation phase, a six degrees-of-freedom electromagnetic locating or tracking system 114, or other suitable system for determining position and orientation of a distal portion of the catheter 102 (e.g., Fiber-bragg flex sensors), is utilized for performing registration of pre-procedure images (e.g., a CT image data set and 3D models derived therefrom) and the pathway for navigation with the patient as they are located on operating table 112.

In an EMN type system, the tracking system 114 may include a tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism. Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P.

Registration refers to a method of correlating the coordinate systems of the pre-procedure images, and particularly a 3D model derived therefrom, with the patient P's airways as, for example, observed through the bronchoscope 108 and allow for the navigation to be undertaken with accurate knowledge of the location of the sensor 104 within the patient and an accurate depiction of that position in the 3D model. Registration may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the 3D model generated in the planning phase, and a location correlation between the shape and the 3D model based on the comparison is determined, e.g., utilizing the software on computing device 122. The software aligns, or registers, an image representing a location of sensor 104 with the 3D model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the 3D model.

Though described herein with respect to EMN systems using EM sensors, the instant disclosure is not so limited and may be used in conjunction with flexible sensor, shape sensors such as Fiber-Bragg gratings, ultrasonic sensors, or without sensors. Additionally, the methods described herein may be used in conjunction with robotic systems such that robotic actuators drive the catheter 102 or bronchoscope 108 proximate the target.

As described in greater detail below, at any point during the navigation process, and as described in greater detail below, a tool such as a biopsy tool, access tool, or a therapy tool including for example microwave ablation tools may be inserted into the catheter 102 to place the tool proximate the desired target.

With respect to the planning phase, computing device 122, or a separate computing device not shown, utilizes previously acquired CT image data for generating and viewing a 3D model or rendering of patient P's airways, enables the identification of a target (automatically, semi-automatically, or manually), and allows for determining a pathway through patient P's airways to tissue located at and around the target. More specifically, CT images acquired from CT scans are processed and assembled into a 3D CT volume, which is then utilized to generate a 3D model of patient P's airways. The 3D model may be displayed on a display associated with computing device 122, or in any other suitable fashion. Using computing device 122, various views of the 3D model or enhanced two-dimensional images generated from the 3D model are presented. The enhanced two-dimensional images may possess some 3D capabilities because they are generated from 3D data. The 3D model may be manipulated to facilitate identification of target on the 3D model or two-dimensional images, and selection of a suitable pathway through patient P's airways to access tissue located at the target can be made. Once selected, the pathway plan, 3D model, and images derived therefrom, can be saved, and exported to a navigation system for use during the navigation phase(s). The ILLUMISITE software suite currently sold by Medtronic PLC includes one such planning software.

An initial aspect of the planning phase relates to tumor monitoring, so called watchful waiting. As part of this, a series of CT image data sets may be acquired of the patient over a period of time (e.g., months or years). With the tumor being identified in each CT image data set. Though described as CT image data sets, any Digital Imaging and Communications in Medicine (DICOM) format image data set may be employed for this purpose. By identifying the contours of the tumor, using the processes outlined herein below, and focusing just on the portion of the CT image data set proximate the tumor, a progression of the disease may be observed. This may be done in video form where the size and shape of the tumor change over time in the video. Alternatively, the tumor boundaries in each CT image data set may be overlaid on each other using for example different colors or different levels of transparency indicating the extent of the progression of the tumor at each imaging. Such boundaries may be depicted in both 2D images and in 3D volumes. Utilizing these features a determination can be made as to which tumor should be treated, and which may be allowed to continue growing to be treated at a later date. Issues such as post therapy pain, proximity to critical structures and the efficacy of systemic therapies such as chemotherapy in lieu of ablation may all play a role in determining which tumors to treat at any given time.

Figure 2A:
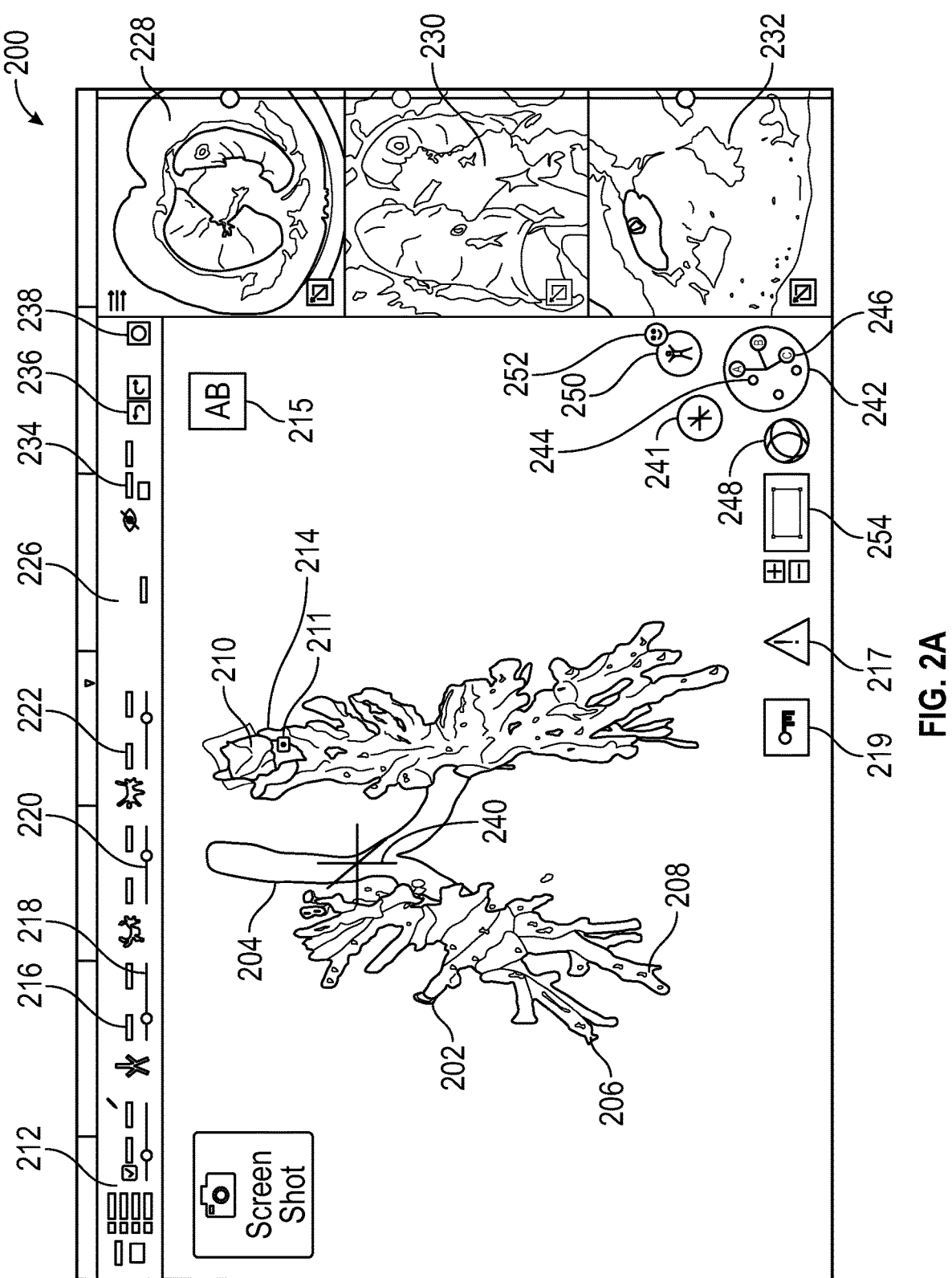
FIG. 2A is an exemplary navigation and treatment planning user interface in accordance with the disclosure.

FIG. 2A depicts a user interface 200 of a 3D modeling and pathway planning system in accordance with the disclosure. The 3D modeling and pathway system includes a software application stored in a memory on computing device 122 that when executed by a processor performs a variety of steps as described hereinbelow to generate the outputs displayed in the user interface 200. As depicted in the center of the user interface 200 one of the first steps of the software is to generate a 3D model 202. The 3D model 202 is of the airways and the vasculature around the airways and generated, for example, from a pre-procedure CT image dataset of the patient's lungs. Using segmentation techniques, the 3D model 202 is defined from the CT image data set and depicts the airways 204 in one color, the veins 206 in a second color, and the arteries 208 in a third color to assist the surgeon in distinguishing the portions of the anatomy based on color.

The application generating the 3D model 202 may include a CT image viewer (not shown) enabling a user to view the individual CT images (e.g., 2D slice images from the CT image data) prior to generation of the 3D model 202. By viewing the CT images the clinician or other user may utilize their knowledge of the human anatomy to identify one or more tumors in the patient. The clinician may mark the position of this tumor or suspected tumor in the CT images. If the tumor is identified in for example an axial slice CT image, that location may also be displayed in for example sagittal and coronal views. The user may then adjust the identification of edges of the tumor in all three views to ensure that the entire tumor is identified. As will be appreciated, other views may be viewed to assist in this process without departing from the scope of the disclosure. The application utilizes this indication of location provided by the clinician to generate and display an indicator of the location of the tumor 210 in the 3D model 202. In addition to manual marking of the location of the tumor, there are a variety of known automatic tumor identification tools that are configured to automatically process the CT image scan and to identify the suspected tumors.

Once the tumor 210 is identified the pathway planning software allows the user to identify an airway proximate the tumor 210 in, for example, a 2D slice of the 3D volume of the CT image data set. When an airway is identified, the pathway planning software may automatically generate a pathway from the tumor, and specifically the identified airway proximate the tumor, to the trachea. This can be achieved using an algorithm that ensures that at every advancement of the pathway from the tumor 210 to the trachea, the diameter of the airway increases relative to the prior portion of the airway. As will be appreciated, the planning software may also automatically identify the closest airway to the tumor 210 and generate the pathway from the tumor 210 to the trachea to be accepted by a clinician.

Further and in connection with methods described below, when the tumor 210 is located outside of the airways, an access point 211 may be either automatically generated or manually identified and displayed in the 3D model 202. The access point 211 is a point on the surface of the airways 204 where an access tool 400 (FIG. 4A), can be employed to pierce the airway and tunnel through the parenchyma and other tissue of the lungs outside of the airways to arrive at the tumor. The identification of the access point 211 considers a number of factors including the flexibility of the catheter 102, the flexibility of the access tool 400, the flexibility of a biopsy tool 500 (FIG. 5), and both the flexibility and bending constraints of an ablation catheter 600 (FIG. 6), the shape of the airway proximate the tumor 210. As will be appreciated, it is desirable to navigate the catheter 102 directly to the tumor before inserting any of the above-identified tools, however, due to the constraints of the diameter of the airways, and the limits of bending of any of the tools, for procedural purposes the access point 211, may be better placed at some distance from the closest point of approach to the tumor that the catheter 102 may achieve. In practice, it is desirable for the access point 211 be located at a point where the access tool 400, biopsy tool 500, or ablation catheter 600 may extend from the airway of the lung, through the access point 211, through the parenchyma, and into the tumor in a substantially straight line such that additional bending of the distal portion of these tools can be limited.

Another factor to consider in determining the placement of the access point 211 is the shape of the airway proximate the tumor 210. As will be appreciated, if there is a sharp bend in the airway and the access tool 400 is deployed, there is a risk that the access tool might slip before piercing the airway and slide down the airway rather than create an opening in the airway. As with other data that is generated pre-procedurally, the access point 211 may be displayed on intra-procedure images (e.g., fluoroscopic or CBCT images) captured by the imaging device 124. Further, once so overlaid on intra-procedure images, the user has the ability to adjust the placement of the access point 211 to account for any differences in the shape of the airways and the lungs between the pre-procedure images and their actual position as found by the intra-procedure images. The updates made by moving the access point 211 to a desired position in the intra-procedure images may be reflected by a change in position of the access point in the 3D model 202 to update the pathway to navigate the catheter 102 to the tumor.

The user interface 200 includes a variety of features that enable the clinician to better understand the physiology of the patient and to either enhance or reduce the volume of information presented such that the clinician is better able to understand. A first tool is the tumor tool 212 which provides information regarding the tumor or lesion that was identified as described above. The tumor tool 212 provides information regarding the tumor such as its dimensions, and depending on the fidelity of the CT images, can provide indicators regarding the toughness or hardness of the tissue of the tumor as compared to the surrounding tissue, as well as the vasculature entering and exiting the tumor 210, as described below. Further, the tumor tool 212 allows for creation of a margin 214 around the tumor 210 at a desired distance from edges of the tumor 210. The margin 214 indicates a portion of healthy tissue that should be removed to ensure that all of the cancerous or otherwise diseased tissue is removed to prevent future tumor growth.

As noted above, by providing an indicator of the margin 214, the user may manipulate the 3D model 202 to understand the vasculature which intersects the tumor 210 and other aspects of the anatomy around the tumor 210. Since tumors are blood rich tissue there are often multiple blood vessels which lead to or from the tumor. Each one of these needs to be identified and addressed during a procedure to ensure complete closure of the blood vessels serving the tumor or to be accounted for as a thermal sink during an ablation procedure, thus necessitating greater power to achieve a complete ablation. Additionally, the margin may be adjusted or changed to limit the impact of the procedure on adjacent tissue that may be supplied by common blood vessels or that is part of a separate lobe or segment of the lungs. As will be appreciated limiting the damage caused by ablation to just those portions of the lung in which the tumor or lesion is manifest is always desirable. For example, the margin is reduced to ensure that only one branch of a blood vessel is transected and sealed, while the main vessel is left intact so that it can continue to feed other non-tumorous tissue. The identification of these blood vessels in an important feature of the disclosure.

An ablation planning feature 215 allows for the automatic generation of a treatment plan based on the location, size, and shape (including margin 214) of the tumor 210, proximity and size of blood vessels, proximity of critical structures (described below), the ablation modality (e.g., microwave, cryogenic, radiofrequency, ethanol, etc.). The ablation planning feature 215 assesses these and other features to output a variety of data including ablation timing, power settings of a generator, duration of pauses in therapy, locations for placement of the ablation catheter in the tumor, order of placements of the ablation catheter in the tumor 210 when multiple placements are needed to ablate the entire tumor 210 or odd shapes of the tumor 210, and an expected ablation zone.

As will be appreciated the ablation planning feature may be fully automatic or may rely on some or all manual inputs based on the user preference. Still further, the ablation planning feature whether automatic or relying on manual inputs can output several options that may be different in approach, including the modality of ablation, and the user may select from the options for providing the therapy to the tumor 210.

Still a further aspect of the ablation planning feature relates to instances where there are multiple tumors that require therapy. As is known, ablation of a tumor causes changes in the shape of the tissue in which the tumor is located. In the case of the lungs, for example, when a tumor is ablated, regardless of the modality, the lungs shrink. The amount of the shrinkage is dependent upon a variety of factors including, the amount of airway tissue in the ablation and the proximity to larger airways. The proximity to the pleura boundary. Other disease states such as COPD and emphysema can also have an impact on the shrinkage. In accordance with the disclosure, once all of the tumors are identified and the therapies determined (e.g., modality, power, size of ablation zone, etc.), the ablation planning feature can calculate the amount of shrinkage each ablation will result in within the body of the patient and estimate the amount of movement each ablation will cause the other tumors within the body. Finally, with the estimated movement calculated, an order of therapy can be determined. In one example, the order of therapy is determined such that each ablation results in a minimum amount of anticipated movement to the remaining tumors. The result is that the ablation planning feature provides a proposed order of therapy to the user. As a general proposition, this will often result in tumors that are in the lower lobes are generally treated first, whereas tumors in the upper lobes are treated second, however, there are factors, as described above, which might result in a different order being recommended.

The next tool depicted in FIG. 2A is an airway generation tool 216. The airway generation tool 216 allows the user to determine how many generations of the airways are depicted in the 3D model 202. As will be appreciated, image processing techniques have developed to allow for the identification of the airways throughout the lung tissue. There are up to about 23 generations of airway in the lungs of a human from the trachea to the alveolar sacs. However, while very detailed 3D models can be generated, this detail only adds to the clutter of the 3D model and renders the model less useful to the user as the structures of these multiple generations obscures structures. Thus, the airway generation tool 216 allows the user to limit the depicted generations of the airways to a desired level that provides sufficient detail for the planning of a given procedure. In FIG. 2A the airway generation tool 216 is set to the third generation, and a slider 218 allows for the user to alter the selection as desired.

Both a venous blood vessel generation tool 220 and an arterial blood vessel generation tool 222 are depicted in FIG. 2. As with the airway generation tool 216, the venous blood vessel generation tool 220 and the arterial blood vessel generation tool 222 allow the user to select the level of generations of veins and arteries to depict in the 3D model 202. Again, by selecting the appropriate level of generation the 3D model 202 may be appropriately decluttered to provide useable information to the user.

While these blood vessel generation tools 220 and 222 and the airway generation tool 216 are described here as being a global number of generations of blood vessels and airways displayed in the 3D model 202, they may also be employed to depict the number of generations distal to a given location or in an identified segment of the 3D model 202. In this manner the clinician can identify a particular branch of an airway or blood vessel and have the 3D model 202 updated to show a certain number of generations beyond an identified point in that airway or blood vessel.

Additional features of the user interface 200 include a CT slice viewer 226. When selected, as shown in FIG. 2, three CT slice images 228, 230, and 232 are depicted in a side bar of the user interface 200. Each of these CT slice images includes its own slider allowing the user to move alter the image displayed along one of three axes (e.g., axial, coronal, and sagittal) of the patient to view portions of the patient's anatomy. The features identified in the 3D model 202 including airways, venous blood vessels, and arterial blood vessels are also depicted in the CT slice images to provide for greater context in viewing the images. The CT slice images may also be synchronized with the 3D model 202, allowing the user to click on any point in the 3D model 202 and see where that point is located on the CT views. This point will actually be centered in each of the CT slice images 228, 230, and 232. Further, this synchronization allows the user to click on any branch in the 3D model 202 and see where that branch is located on the CT slice images 228, 230, 232. An expand icon 233 in the lower left-hand corner of each CT slice image 228, 230, 232 allows the CT slice image to replace the 3D model 202 in the main display area of the user interface 200.

A hidden tissue feature 234 allows for tissue that is hidden from the viewer in the current view of the 3D model 202 to be displayed in a ghosted or outlined form. Further, toggles 236, and 238 allow for the 3D model 202 to be flipped or rotated.

A critical structures feature 217 may be employed by the user to identify certain critical structures that appear in the 3D model. By selecting the critical structures feature 217, the user may manipulate the user interface and mark a variety of critical structures. Once accepted, these critical structures are saved as well as their relative locations and orientations for later application as an overlay on intraprocedural images. The critical structures may include certain blood vessels proximate the tumor or the access point 211, nerves, other tissue to be avoided. The blood vessels may, for example, be ones that must be avoided during the piercing of the airway using the access tool 400 or during a biopsy to prevent undesired bleeding within the patient. Alternatively, because blood vessels also act as a heat sink during an ablation procedure, in addition to avoiding piercing the blood vessel, the energy applied to the tumor to achieve a successful ablation needs to be increased, or the placement of the ablation catheter 600 may need to be adjusted so that an ablation zone fully captures tumor, the margins around the tumor are consistent, and tissue such as the blood vessels themselves are not unnecessarily damaged. The location of these critical structures in the 3D model 202 can be overlaid on intraprocedural fluoroscopic or CBCT imaging captured by imaging device 124, as will be described in greater detail below. As will be appreciated, the overlaying of data from pre-procedural images and 3D models derived therefrom requires a registration process such as that described above, to properly place data from the pre-procedural images into the correct position and orientation of structures seen in the intra-procedural images.

In addition to a critical structures feature 217, a separate related set of structures may be identified in the pre-procedure images and depicted on the 3D model 202, these are key structures. Again, a key structure feature 219 may be selected and the user may mark key structures by manipulating the user interface 200. Once accepted, these key structures are saved as well as their relative locations and orientations for later application in registration, divergence determination, and as an overlay on intraprocedural images. These key structures may be for example the outline of the airways, the position of certain bifurcations, the location of the tumor, an outline of the location of the pleura boundary, and others. As will be described in greater detail below, these key structures can be used overlaid on intra-procedural images to determine divergence from the pre-procedure images to the position of the structures within the patient.

In addition to the foregoing, there are a variety of tools that are enabled via the UI 200. These tools may be in the form of individual buttons that appear on the UI 200, in a banner associated with the UI 200, or as part of a menu that may appear in the UI 200 when right or left clicking the UI 200 or the 3D model 202. Each of these tools or the buttons associated with this is selectable by a user employing the pointing device to launch features of the application described herein.

Additional features of the user interface 200 include an orientation compass 240. The orientation compass provides for an indication of the orientation of the three primary axes (axial, sagittal, and coronal) with respect to the 3D model. As shown the axes are defined as axial in green, sagittal in red, and coronal in blue. An anchoring tool 241 when selected by the user ties the pointing tool (e.g., mouse or finger on touch screen) to the orientation compass 240. The user then may use a mouse or other pointing tool move the orientation compass 240 to a new location in the 3D model and anchor the 3D model 202 in this location. Upon release of the pointing tool, the new anchor point is established and all future commands to manipulate the 3D model 202 will be centered on this new anchor point. The user may then to drag one of the axes of the orientation compass 240 to alter the display of the 3D models 202 in accordance with the change in orientation of the axis selected.

A related axial tool 242 is can also be used for to change the depicted orientation of the 3D model. As shown axial tool 242 includes 3 axes axial (A), sagittal (S), coronal (C). Though shown with the axes extending just to a common center point the axes extend through to the related dot 244 opposite the dot 246 with the lettering. By selecting any of the lettered or unlettered dots the 3D model be rotated automatically to the view along that axis from the orientation of the dot 244 or 246. Alternatively, any of the dots 244, 246 may be selected and dragged and the 3D model will alter its orientation to the corresponding viewpoint of the selected dot. In this way the axial tool 242 can be used in both free rotation and snap modes.

A single axis rotation tool 248 allows for selection of just a single axis of the three axes shown in the orientation compass 240 and by dragging that axis in the single axis rotation tool 248, rotation of the 3D model 202 is achieved about just that single axis. Which is different than the free rotation described above, where rotation of one axis impacts the other two depending on the movements of the pointing device.

A 3D model orientation tool 250 depicts an indication of the orientation of the body of a patient relative to the orientation of the 3D model 202. A reset button 252 enables the user to automatically return the orientation of the 3D model 202 to the expected surgical position with the patient lying on their back.

A zoom indicator 254 indicates the focus of the screen. By default, the inner white rectangle will be the same size as the outer grey rectangle. As the user zooms in on the 3D model 202, the relative size of the white rectangle to the grey indicates the level of zoom. In addition, once zoomed in, the user may select the white rectangle and drag it left or right to pan the view of the 3D model displayed in the user interface 200. The inner white rectangle can also be manipulated to adjust the level of the zoom. The plus and minus tags can also be used to increase or decrease the level of zoom.

Figure 3:
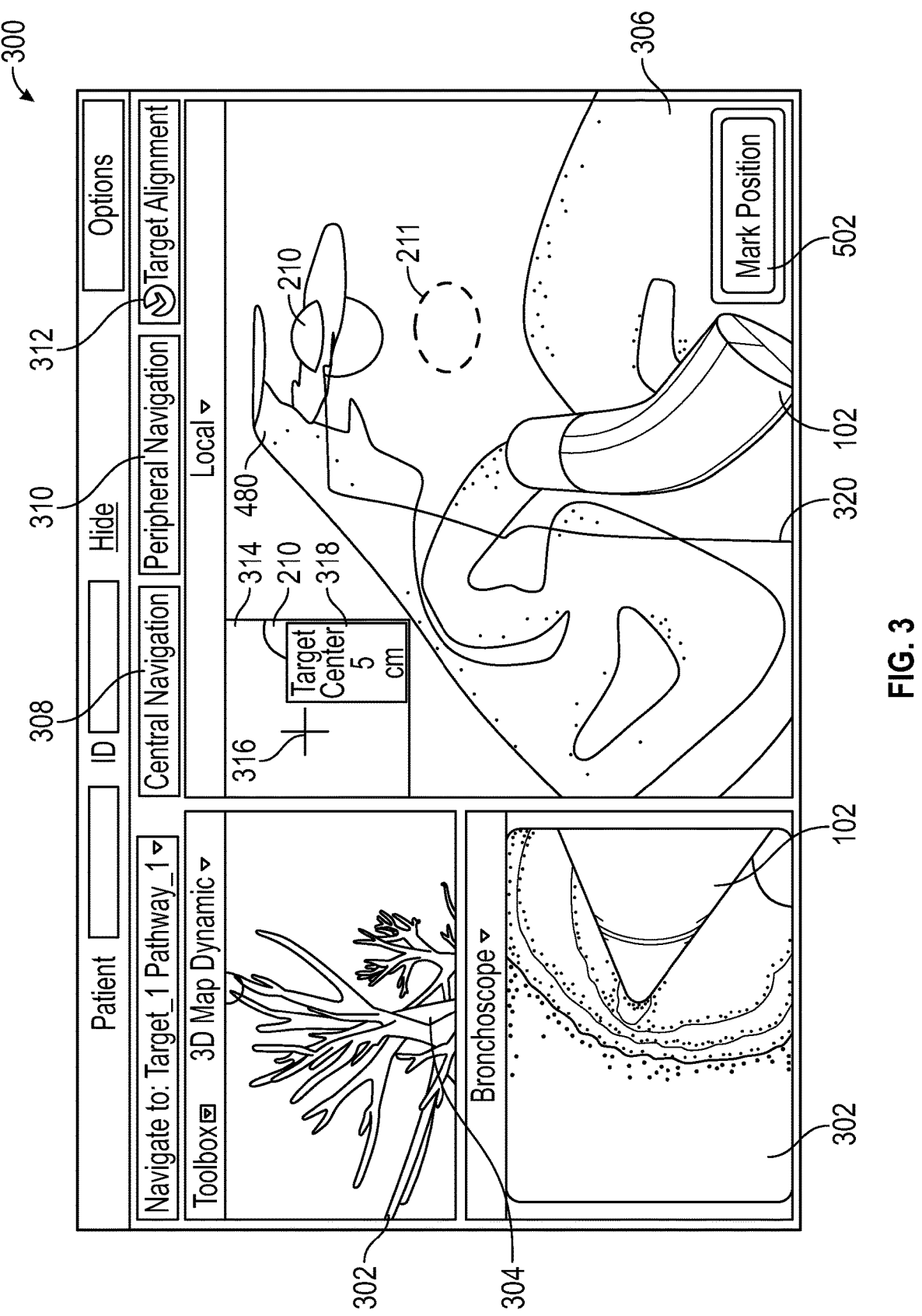
FIG. 3 is a user interface for intraluminal navigation in accordance with the disclosure.

After identifying a tumor 210, determining a pathway to the tumor, identifying access points 211, critical structures and key structures and establishing an ablation plan including an order of therapy if multiple tumors are being treated, all of that data can be used by the computing device 122 to enable guided navigation of the catheter 102 to the tumor 210. As noted above, the first step of such navigation is registration of the 3D model 202 and therewith the data identified above, with the patent P as they are located on the operating table 112. Following registration of the patient P to the image data and pathway plan, a user interface 300 as shown in FIG. 3 is displayed on the computing device 122 allowing the clinician to advance the catheter 102 into the airways of the patient P hand have the movements of the catheter 102 be replicated in the 3D model 202.

Figure 2B:
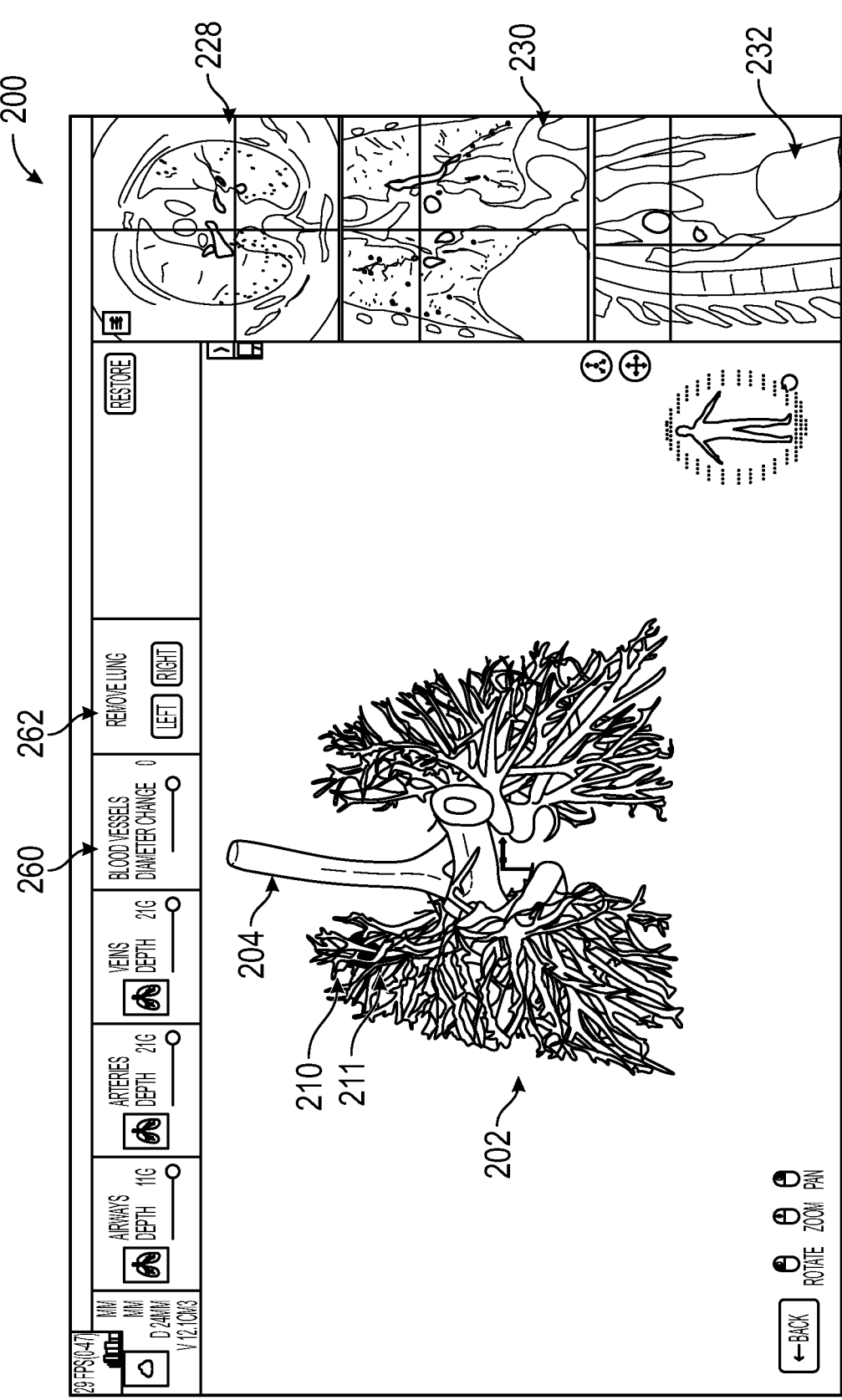
FIG. 2B is a second exemplary navigation and treatment planning user interface in accordance with the disclosure

FIG. 2B depicts an alternative UI 200 for planning a navigation of a catheter 102 into the airways of a patient. The UI 200 may be better suited in certain circumstances for determining where to place the access point 211 so that the catheter 102 may be navigated to the tumor 210. As can be seen, and described in greater detail below, the placement of the access point 211 at a location where the airway can be pierced but the blood vessels are substantially spared from any trauma is an important aspect of the disclosure. The attributes for placement of the access point 211 include good avoidance of blood vessels, avoidance of other critical and key structures, at a location where the access point 211 can be reached without extreme bends to the access tool 400, and the ability to reach the tumor 210 by advancing the access tools 400 in a substantially straight line. It is also desirable, when possible, to avoid piercing multiple segments or lobes of the lung when piercing the airway wall. All of these factors can be assessed by manipulating the 3D model 202 and adjusting the displayed parameters.

FIG. 2B has two additional features not shown in FIG. 2A. A blood vessel diameter feature 260 enables the user to determine the minimum size of the blood vessels to be displayed in the 3D model 202. By eliminating the smallest blood vessels, or some portion of the blood vessels that are smaller than a certain size the 3D model becomes much less crowded, and the tumor and airways become more visible. Further, the option to remove one of the lungs from the 3D model with the selector 262 further reduces the clutter of the 3D model. Both of these features make it easier to assess the access point 211 and determine where it should be optimally placed as well as enabling more thorough review of the aspects of the 3D model the user believes is most important for their purposes.

The user interface 300 includes a variety of features that are common to lung navigation applications. These include a bronchoscopic view 302 depicting the view from a bronchoscope, where one is employed. A 3D map view 304 provides a perspective view of the location of the catheter 102 as it is navigated through the patient P and the 3D model 202. A variety of toggles enable changing the primary view 306 displayed in the user interface 300. These include a central navigation toggle 308, a peripheral navigation toggle 310 and a target alignment view 312. As the navigation of the catheter 102 changes from the central airways to the peripheral airways the appropriate toggle may be selected to change the main view 306. This may also be automatic as the location of the catheter 102 is detected. As shown in FIG. 3, the target alignment view 312 has been selected. Once selected a target window 314 is displayed. The target window 314 depicts crosshairs 316, the target 210 and a distance indicator 318 displaying the distance from the detected location of the end of the catheter 102 and the tumor 210. As shown in the user interface 300 of FIG. 3, the catheter 102 has been navigated to within about 5 cm of the tumor 210. Also depicted in the main view 306 is the planned pathway 320 to the target 210.

As noted above, in instances where the tumor 210 is located outside of the airways of the patient, an access tool 400 is required to pierce the airway to provide access for the catheter 102 and other tools that may be passed through the catheter 102 to act on the tumor 210. Also shown in FIG. 3 is the access point 211 which, as described above, provides a substantially straight path to the tumor and through which an access tool should be inserted to ensure access to the tumor 210. As shown the access point 211, as depicted in the user interface 300 is not on the planned pathway. This may be intentional or may indicate a divergence as described herein requiring local registration of the tumor 210 and the sensed location of the catheter 102 to correct. In addition, following local registration, the location of the access point 211 may be updated via for example the user interface 300 before employing the access tool 400 to reach the tumor 210.

Figures 4A, 4B:
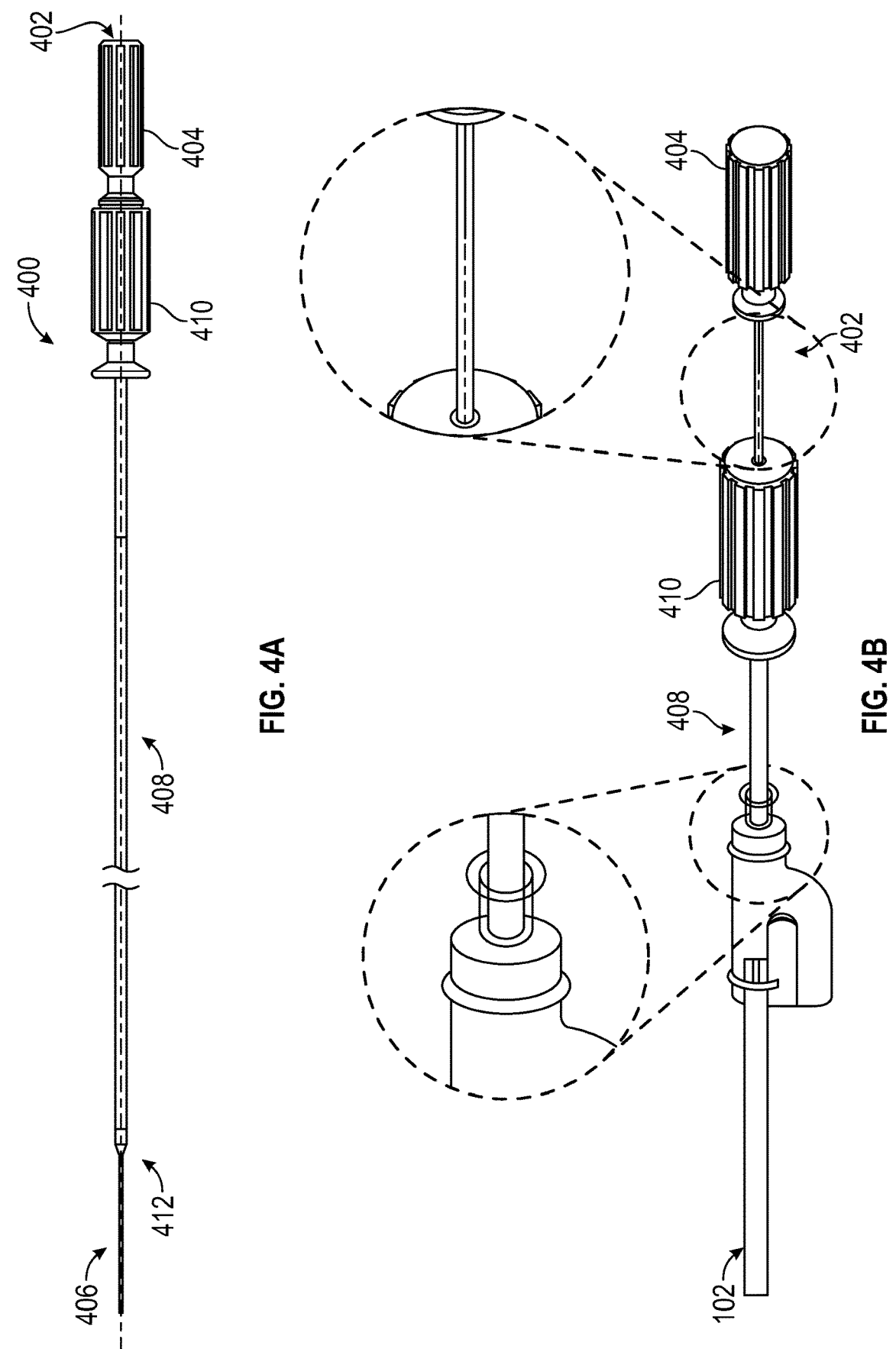
FIG. 4A is a perspective view of an access tool in accordance with the disclosure.
FIG. 4B is a perspective of the access tool of FIG. 3A as it is inserted and manipulated in a catheter.

An example of the access tool 400 is depicted in FIGS. 4A and 4B and is sized to be received in the catheter 102. The access tool 400 includes a piercing member 402 having a handle 404 at one end and a piercing tip 406 at the opposite end. In one embodiment the piercing member 402 and piercing tip 406 are formed of a wire (e.g., stainless or nitinol) having sufficient rigidity to pierce an airway wall.

The piercing member 402 is received in a dilating member 408. The dilating member 408 has a handle 410 on one end and a minimally traumatic end 412. The minimally traumatic end 412 may bullet-shaped, tapered. or another blunt shape that is designed to expand openings in the airway wall formed by the piercing tip 406, but not itself pierce tissue. The minimally traumatic end 412 may be formed of a metal such as stainless steel. At maximum insertion the piercing tip 406 of the piercing member extends about 5 CM beyond the minimally traumatic end 412 of the dilating member 408. In FIG. 4A the piercing member 402 is shown fully advanced through the dilating member 408 such that the wire extends beyond the minimally traumatic end 412, and the handle 404 of the wire abuts the handle 410 of the dilating member 408.

Both the piercing member 402 and the dilating member 408 are flexible and configured for insertion into a lumen of catheter 102 which may act as an extended working channel of the bronchoscope 102 in which it is inserted enabling placement proximate endobronchial lesions, peripheral lung nodules, or lung masses. The piercing member 402 extends through the inner lumen of the dilating member 408 and can be manipulated independently from the dilating member 408 using the handle 404 to puncture the airway wall to create a passage from within the airway to a tumor 210 location outside of the airway.

Once the opening is formed in the airway wall with the piercing member 402, the dilating member 408 is advanced over the piercing member 402 to expand the opening in the airway wall and to dissect tissue beyond the airway wall to create a pathway to the tumor 210. Upon arriving at the tumor 210, the catheter 102 can be slid over the dilating member 408 such that the catheter 102 is immediately adjacent the tumor 210, or even within the tumor 210. To assist with the multiple handles 404, 410, a rail system may be employed allowing for the independent manipulation and advancement of the handles.

Prior to piercing the airway wall at the access point 211, a local registration may be undertaken. The local registration is useful in eliminating any divergence such as CT-body divergence, but also any divergence in the position of the tumor 210 caused by shrinkage related to therapy of other tumors 210, the insertion of tools into the airways, and the position of the patient P. A local registration employs imaging device 124 to acquire intra-procedure images of the area proximate the end of the catheter 102 and the tumor 210. An initial step is to acquire a 2D fluoroscopic image of the catheter 102 and mark the area of the catheter 102. This helps to ensure that the imaging device is properly focused on the catheter 102. Next, a sequence of fluoroscopic images is captured by the imaging device 124 for example from about 25 degrees on one side of the AP position to about 25 degrees on the other side of the AP position and a fluoroscopic 3D reconstruction may be then generated by the computing device 122. The generation of the fluoroscopic 3D reconstruction is based on the sequence of fluoroscopic images and the projections of structure of markers incorporated with transmitter mat 120 on the sequence of images. Following generation of the fluoroscopic 3D reconstruction, the catheter 102 needs to be marked in two 2D images of the 3D reconstruction. The two images are taken from different portions of the fluoroscopic 3D reconstruction. The fluoroscopic images of the 3D reconstruction may be presented on the user interface in a scrollable format where the user is able to scroll through the slices in series if desired. Next the tumor needs to be marked in fluoroscopic 3D reconstruction. A scroll bar may be provided to allow the user to scroll through the fluoroscopic 3D reconstruction until the tumor is identified. In addition, the tumor 210 may need to be marked in at two different perspectives. Once complete, the user-interface displays the entire fluoroscopic 3D reconstruction which may be viewed slice by slice to ensure that the target or lesion remains within the marker through the fluoroscopic 3D reconstruction.

After confirming that the tumor 210 has been accurately marked the local registration process ends and the relative position of the catheter 102 in the 3D model 202 and the pathway plan is updated to display the actual current relative position of the end of the catheter 102 and the tumor 210 as it is in the patient.

With the position of the tumor 210 updated the position of the access point 211 relative to the tumor 210 can be assessed by user and if desired updated based on the criteria described above. To assist in this assessment, the critical structures may be depicted in the 3D model to ensure for example that the new location of the access point would not interfere with blood vessels and the like based on the updated position of the tumor 210.

Once the access point 211 is updated, the airway may be pierced using the access tool 400 as described above may be advanced through the opening created and the catheter 102 may be advanced over the access tool 400 until it is proximate the tumor 210.

Referring back to the ablation planning feature, all of the data generated pre-procedurally related to the placement of the ablation catheter 600, the timing and power settings of the ablation and the duration of any pauses can be presented on the user-interface for the clinician as they are preparing to initiate the therapy portion of the procedure. In addition, this data can be overlaid on intraprocedural images (e.g., fluoroscopic or CBCT images). These may be additional intraprocedural images acquired after the local registration. As an example, the place for insertion of the catheter 102 into the tumor 210 can be overlaid on the intraprocedural images so that placement is accurate prior to insertion of an ablation catheter. In some instances, the intraprocedural images may be live fluoroscopic video such that the advancement of the catheter 102 into the tumor 210 can be observed as the catheter 102 intersects with the overlaid marked location from the ablation planning feature.

Once properly placed, and again before insertion of the ablation catheter 600, the ablation zone specified in the ablation planning feature can be overlaid and compared to the tissue as it presents itself in the intraprocedural images. As is known, the position of tissue during the procedure is expected to be different from its position during pre-procedure images. Indeed, this is the rationale for the local registration. Thus, by overlaying the anticipated ablation zone on the intraprocedural images the user may edit the ablation zone prior to insertion of the ablation catheter 600 into the catheter 102 and tumor 210. For example, the margin may be altered or the placement of the catheter 102 may be adjusted to alter the planned ablation in situ with a visual representation of the expected ablation zone.

Further, as the ablation catheter 600 is inserted into the catheter 102, a further set of intra-procedural images may be acquired from imaging device 124. At this point the ablation catheter may be segmented from the images to confirm placement in the correction location and at the correct depth in the tumor 210 and the anticipated ablation zone, as updated or altered can be overlaid onto these images prior to initiating the ablation. This provides one more opportunity to adjust or alter the ablation zone, the margin, the placement of the ablation catheter, the power, duration, and other factors prior to in initiating therapy. Once the ablation zone, as it is overlaid on the image of the tumor 210 in the intraprocedural image, is deemed acceptable, the therapy may be commenced (e.g., application of microwave energy, RF energy, etc.).

With respect to the key structures that were identified above, by observing the overlay of these key structures on the intra-procedure images (e.g., fluoroscopic or CBCT images) acquired by the imaging device 124 monitoring of the lungs can be undertaken during the procedure. This monitoring can be either manual or automatic and enables determination of a level of divergence between the position of these key structures in the pre-procedure images and 3D model to the intra-procedure images. That divergence may be a result of movement of the patient or the result of some intra-procedural aspects such as insertion of one or more of the catheters 102, or tools such as the access tool 400 or the ablation catheter 600 through the catheter 102. Further, the divergence may be an indicator of atelectasis in one or more lobes of the lung or movement of the tumor. As a result of this detected divergence, an indicator may appear on the user interface directing the user to undertake another scan either with the imaging device 124 or the same imaging modality of the pre-procedure imaging to confirm the divergence and assess the changing conditions of the anatomy of the patient.

As noted herein, a variety of intraprocedural imaging may be employed during the treatment of a patient. One aspect of this disclosure is the ability to register the pre-procedure CT images and any intraprocedural images. In some instances, this allows data from the planning phase to be overlaid on fluoroscopic images. Additionally, in the case of any intraprocedural CT imaging, including CBCT imaging, all of the pathway plan and ablation plan can be brought from one such CT image data set to a second CT image data set based on the registration. This eliminates the need for additional planning being needed interprocedurally. The registration may be based on the structure of the airways, as well as other harder less movable tissues such as ribs that are observable in the CT images. Where appropriate additional local registration as described above may also be employed to eliminate any errors in the registration at or near the tumors 210.

With respect to the intraprocedural imaging using imaging device 124, a variety of techniques are contemplated in connection with the disclosure. As noted above the imaging device 124 may be a fluoroscope or a CBCT imaging device. In instances where imaging device 124 is a CBCT device, the local registration process described above, for updating the position of the catheter 102 relative to the tumor 210 within the patient can also be employed. In one aspect of this application, a low dose CBCT scan can be utilized since a high-resolution scan is not required for the local registration. The low dose scan reduces the amount of radiation that the patient P absorbs during the procedure. It is always desirable to reduce the amount of radiation both the patient P and the doctors and nurses are exposed to during a procedure. In some instances, where there is integration between the imaging device 124 and the system 100, the imaging device 124 may receive input directing the imaging device 124 to specific locations to conduct the imaging.

Further aspects of the intraprocedural imaging are related to additional means of reducing the amount of radiation the patient. CBCT imaging devices have a frame rate at which images are captured. By capturing images at relatively high frequency and at small angular displacement between the images, a very high-resolution image data set can be captured by the CBCT imaging device. However, such high-resolution is not required in all instances, as noted above. One aspect of the disclosure is directed to directing the CBCT imaging device 124 to skip frames. Depending on the setting, this could be skipping every other frame, every third frame, every forth frame, etc. By doing so, when considering the hundreds or even thousands of frames which make up a CBCT image, the overall exposure to radiation can be reduced.

Alternatively, particularly where a high-resolution image is desired, for example the placement of the catheter 102 or ablation catheter within the tumor 210 focusing the imaging device 124 onto just the tissue of interest. The rays of the CBCT imaging device 124 can be collimated to narrow the area of imaging to just the tissue or area of interest and not the entire lung of the patient. In this way, the amount of total radiation and the area that the radiation is directed are both reduced. Yet, the images produced from this focused imaging has a very high resolution allowing for detailed analysis and determination of, for example, proper placement of the catheter 102, ablation catheter, tissue around the tumor 210. Where appropriate the ablation zone, the determination of which is described above, can be overlaid this high-quality image data set so that it can be assessed for margin, proximity to critical or key structures, and other factors.

While the preceding aspects are directed at reducing the radiation exposure of the patient P and the clinicians, in some instances that cannot be avoided, or the benefits of the increased exposure outweigh the negative aspects. For example, once the ablation catheter is placed in the tumor 210 the imaging device 124 can be initiated (either manually or automatically) and while the ablation proceeds (e.g., the application of microwave or RF energy). As the ablation proceeds and the tissue desiccates its appearance in the CBCT images changes. These changes in appearance can be tracked as the energy is applied and viewed in real-time during the ablation. Further, the modeled ablation zone can be overlaid on the CBCT images and compared to the progression of the actual ablation. As a result, the actual ablation can be compared to the modeled ablation zone. In addition, an amount of shrinkage or structure movement in the given area of the imaging may be detected and determined and used to update the 3D model 202 for navigation to the remaining tumors.

The pre-procedure CT images that are acquired to perform the planning of the planning of the procedure are typically taken while the patient P is in a breath hold condition. This ensures that the lungs are fully inflated providing greater clarity of images. However, during a procedure, the patient P is typically maintained in tidal volume breathing. This minimizes stress on the patient P, ensuring adequate oxygen saturation during the procedure, and minimizes the movement of the lungs and therewith the tumor 210 as a result of breathing. In connection with both biopsy and ablation, rather than continue at with tidal volume breathing during the ablation or even during the insertion of the ablation catheter insertion into the tumor 210, the imaging can be triggered at a specified positive end-expiratory pressure (PEEP), that is the positive pressure that will remain in the airways at the end of the respiratory cycle. The imaging may be performed at either inspiration or expiration at the predetermined PEEP or may be conducted during a breath hold at the predetermined PEEP. The result is that at the time of insertion ablation catheter, accurate imagining may be acquired with limited movement of the tumor 210 and the ablation catheter during the insertion. The imaging device 124 may be configured to automatically initiate imaging as the lung pressure approaches the specified PEEP and terminate imaging after reaching some threshold lung pressure. In this manner, the CBCT imaging device 124 may be cycled on and off during the ablation procedure at specified times where the tumor 210 is expected to be in the same position. This allows for a consistent comparison of the ablation volume to the tumor 210 and the planned ablation volume.

As will be appreciated integration of the controls of the imaging device 124 and the lung navigation UI 300 can greatly enhance the functionality of the overall system. For example, one or more toggles or buttons may be generated by an application stored in the memory of the computing device 122. Those buttons transmit signals to the imaging device 124 to for example initiate imaging of the patient. In addition, the buttons may transmit signals to the imaging device 124 to control its position relative to the patient. In one embodiment, the position and orientation of the distal portion of the catheter 102, that is known to the navigation application, for example via the interaction of the sensors 104, 126 and the transmitter board 120. This position information can be employed to generate a signal that is transmitted to the imaging device 124 to orient the imaging device 124 in such a way that the images generated are centered on the catheter 102. In instances where the catheter 102 has been navigated proximate the tumor 210, the centering of the imaging on the catheter 102 ensures that the tumor 210 is visible in the images.

As an example, having determined the position of the catheter 102, the navigation application presents on the UI one or more buttons to drive the imaging device 124 to an optimal position for imaging the end of the catheter 124 and the tumor 210. Once so positioned, the imaging device 124 performs the scan, and then transmits the acquired images to the navigation application to display the acquired images or a 3D model generated from the images and updating the navigation UI 300 as described elsewhere herein.

Though described herein as being executed through the use of one or more buttons displayed on the UI 300, the disclosure is not so limited. In contrast, the process may be completely automated and the signals to the imaging device 124 may be generated upon reaching certain milestones during the navigation. For example, upon navigating the catheter 102 proximate the tumor 210, the signal to drive the imaging device 124 to a desired location can be automatically initiated.

Figure 5:
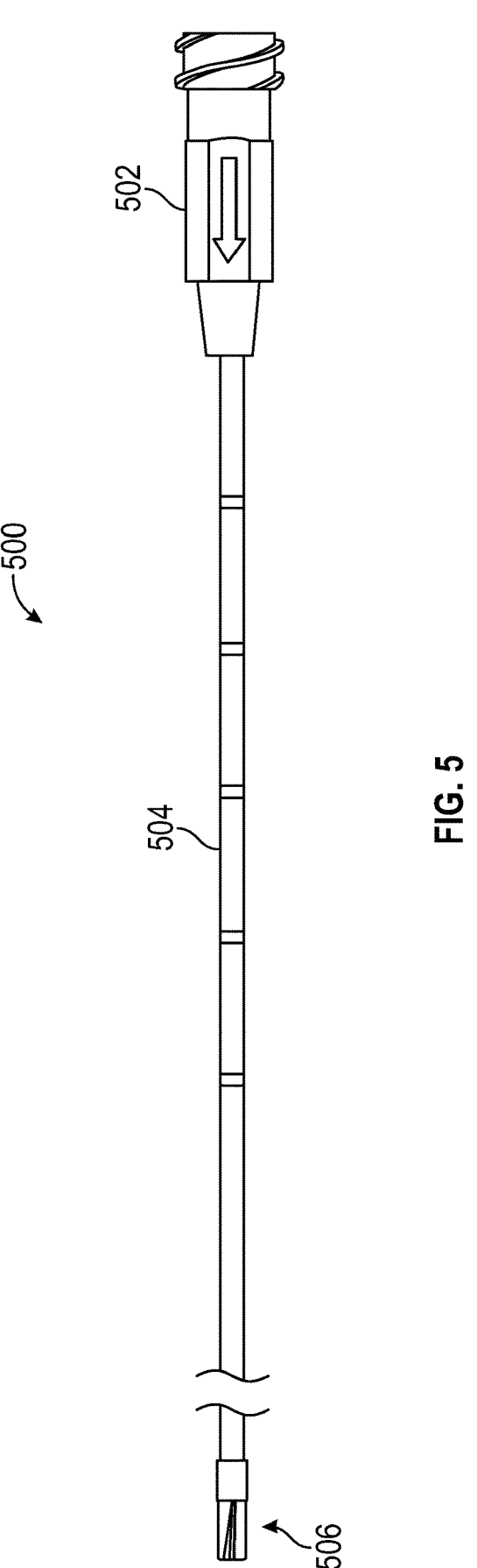
FIG. 5 is a perspective view of a biopsy tool in accordance with the disclosure.

An example of the biopsy tool 500 for use with the systems and methods described herein can be seen in FIG. 5. The biopsy tool 500 includes a handle 502 formed on one end of a catheter 504. The catheter 504 is sized to be received within the navigation catheter 102. In some instances, the biopsy tool is placed in the navigation catheter 102 after the access tool 400 has been utilized as described above, and the distal end of the navigation catheter 102 has been placed either proximate or within the tumor 210. The handle 502 allows the catheter 504, which is flexible, to be forced down the navigation catheter 102. A cutting tip 506 formed on a distal end of the catheter 504. Manual manipulation of the handle 502 translate to manipulation of the cutting tip 506 so that a sample of the tumor 210 can be severed and collected within the biopsy tool 500 for analysis.

As described herein, the methods and systems are in some aspects related to placement of tools, specifically ablation tools in a lesion or tumor of a patient. In particular the ablation tools are navigated through the luminal network of the airways and placed within the tumor or lesion to ablate or kill the cells of the lesion or tumor and a margin around the lesion or tumor to stop the growth of the disease at that location. The EMPRINT™ ablation platform offered by Medtronic is one system for performing an ablation that produces spherical ablations. Other ablation systems such as radio frequency (RF), ethanol, cryogenic, and others may be used with the systems and methods described herein, and the navigation is substantially as described herein above.

Figure 6:
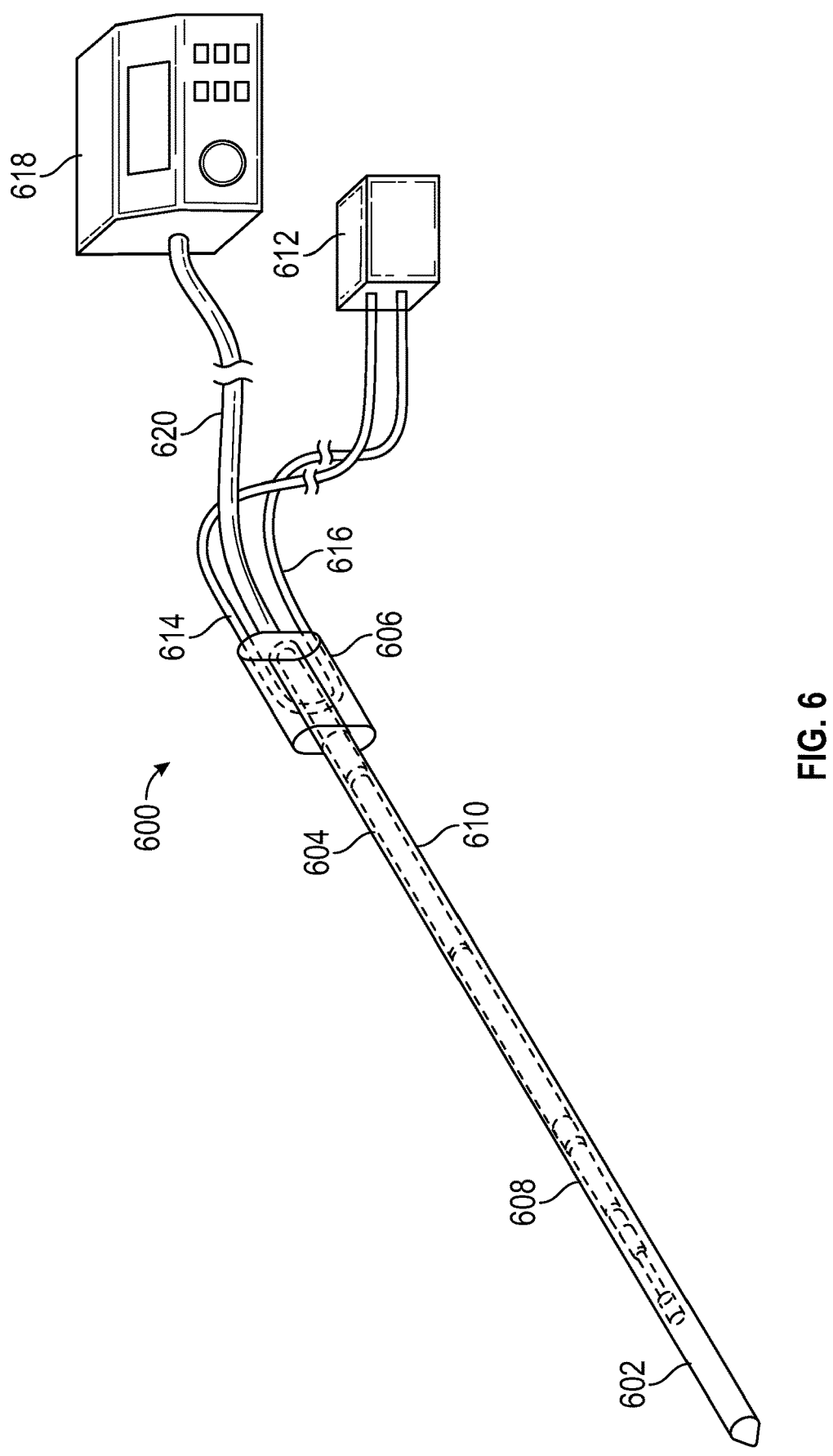
FIG. 6 is a microwave ablation systems in accordance with the disclosure.

FIG. 6 depicts a detailed view of the structure of the microwave ablation probe 600 proximate the distal tip 602. A feedline 604 connects a hand piece 606 to a radiating section 608 near the distal tip 602. The feedline 604 and radiating section 608 are encompassed in a water jacket 610. The water jacket 610 allows for the circulation of water through the ablation probe 600 to help maintain a field dielectric constant throughout the treatment process. The water jacket 610 is connected to a pump 612 that forces water (or saline) through an inlet tube 614 connected to an inlet side of the water jacket 610 and receives water from an outlet side of the water jacket via an outlet tube 616. A microwave generator 618 is connected to the handpiece 604 and specifically the feedline 604 via a cable 620 to enable the transfer of microwave energy from the generator 618 to the radiating section 608. As will be appreciated, the methods and systems described herein are directed to placement of the radiating section 608 at a proper location within the lesion or tumor so that upon application of sufficient energy for an appropriate duration, the cells that make up the tumor or lesion are denatured along with a desired margin of healthy cells which surround to the tumor ensuring that the tumor cannot return at the same location because seed cells have been left behind following the ablation.

Figure 7A:
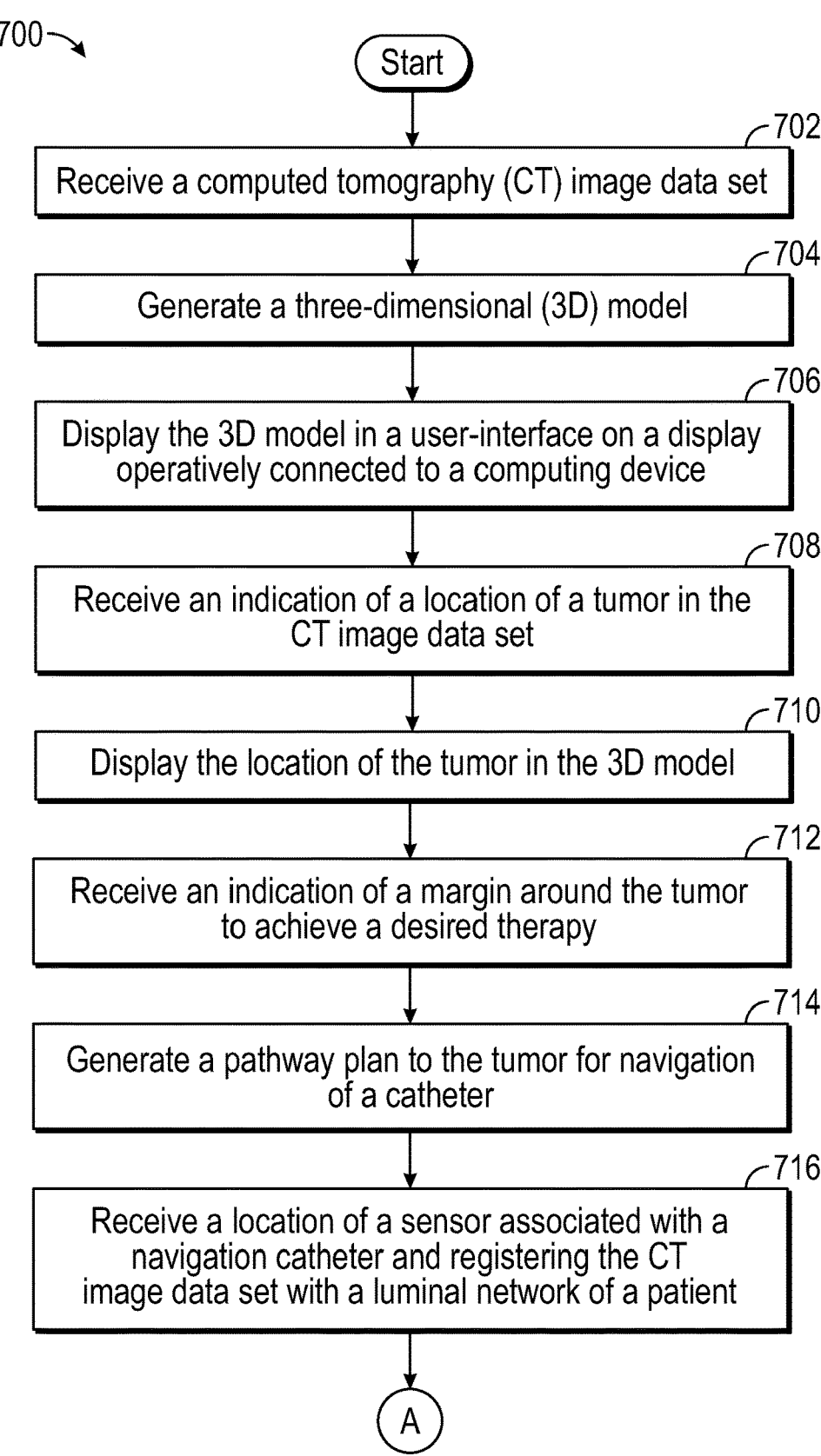
FIGS. 7A and 7B depict a method in accordance with the disclosure.
Figure 7B:
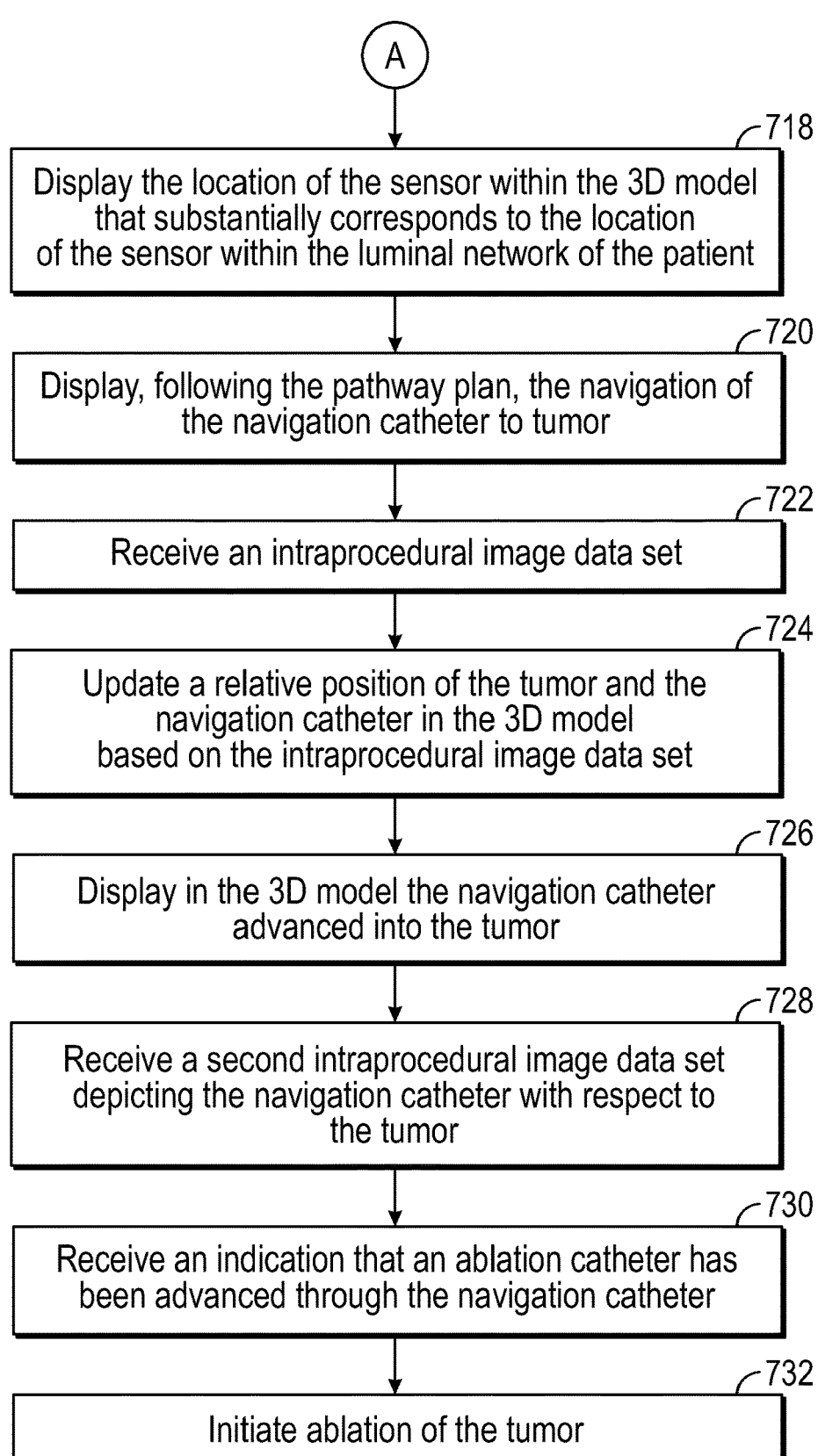

Though described throughout the specification, FIGS. 7A and 7B describe an exemplary method of use of the systems described herein. Those of skill in the art will recognize that one or more of the steps of the method described in FIGS. 7A and 7B may be omitted without departing from the scope of the disclosure. The method 700 starts with receiving a CT image data set at step 702. From that CT image data set a 3D model 200 is generated at step 704. The 3D model 200, and individual CT images (e.g., coronal, axial, sagittal views) can be displayed in a user interface allowing a user to manually inspect them and to determine the location of a tumor 210 at step 706. Alternatively, the software associated with the application performing the method may automatically detect the tumor 210. At step 708 the system receives an indication of the location of the tumor 210. This may be the result of manual marking by a user manipulating the 3D model or CT images in the user interface 200, or it may be the result of a user accepting as accurate an automatic identification of a tumor by the application. Once the indication is received the tumor 210 is displayed on the user interface 200 at step 710. At step 712 an indication of a margin 214 is received and is displayed on the user interface 200. The margin may be the result of manual marking of the margin 214 by inspecting the tumor 210 and the surrounding vasculature and other structures and drawing a line indicating an appropriate margin to capture sufficient healthy tissue and avoid any critical structures. Additionally or alternatively, the margin 214 may be automatically generated by the application and accepted or modified by the user. Next at step 714 a pathway to the tumor 210 may be generated. As an example, the closest airway to the tumor 210 may be identified and once identified, a pathway from that closest airway to the trachea may be automatically generated. Once and both the location and pathway to the tumor 210 are identified the user is ready to conduct a procedure.

At step 716, following placement of a patient P on an operating table 112, and insertion of a catheter 102 and an associated sensor 104, 126 into the airways of the patient P, the application receives a signal from the sensor 104, 126 which indicates its position. Receipt of many such locations as the catheter 102 is moved through at least a portion of the airways enable registration of the 3D model 212 with the patient's actual lungs as they are presented on the operating table 112. Once the patient's lungs are registered to the 3D model 212 and CT image data set, the location of the catheter 102 and particularly the sensor 104,126 is displayed in the 3D at step 718. This displayed position will substantially correspond to the actual location of the catheter 102 within the lungs of the patient. As the catheter 102 is advanced into patient P, the position of the sensor 104,126 is displayed following the pathway plan to navigate the catheter 102 to the tumor 210 at step 720. Once proximate the tumor 210, the imaging device 124 may be deployed and intraprocedural images captured and transmitted to the application at step 722. These intraprocedural images can be employed to determine the relative positions of the catheter 102 and sensor 104, 126 with the tumor 210. At step 724 the relative position of the catheter 102 and the tumor 210 is updated in the 3D model 202. Next as navigation is continued until the catheter 102 is proximate or even within the tumor 210, this navigation of the catheter is displayed on the user interface 200 at step 726. Once the catheter is placed proximate or within the tumor 210 a second intraprocedural image data set is received showing the actual placement of the catheter 102 within the tumor. Data from the procedure planning phase may be overlaid on the tumor 210 including the margin 214 or an expected ablation zone. At this point the parameters of the ablation procedure, which may have been initially determined in the planning stage can be adjusted to adjust the ablation zone to avoid any inconsistencies between the planned ablation and the patient's physiology as it is presented during the procedure can be adjusted accordingly. This may include moving catheter 102, if necessary, to a better location within the tumor 210 to achieve the desired ablation or to avoid the critical structures. After adjusting the ablation parameters as appropriate, an ablation catheter 600 is inserted through the catheter 102 and a signal is received by the application indicating that the ablation catheter 600 has been inserted through the catheter 102 (i.e., to the proper location to achieve the desired ablation zone) at step 730. Once so positioned the ablation or the tumor 210 can be initiated.

A further aspect of the disclosure is directed to the integration of the ablation system 600 and particularly the control of the generator 618 via for example the user-interface 200, 300. For example, upon navigation of the catheter 102 proximate the tumor 210 and undertaking intraprocedural imaging (e.g., step 728), an in vivo assessment of the tumor 210, the proposed margin 214, and any critical structures near or traversing the tumor 210. In this manner, changes to the margin 214 may be made on the user-interface 200, 300. Further, the change in the margin may change the ablation parameters (e.g., increase or decrease in power or duration). These parameters may be automatically calculated by an ablation application stored in the memory of the computing device 122. In addition, the user-interface 200, 300 may enable the initiation and cessation of an ablation procedure via selectable buttons that appear on the user-interface 200, 300 and displayed on the display of the computing device 122.

As noted above, the margin 214 may be manually or automatically determined. An aspect of the automatic determination of the margin 214 is an image analysis of the tumor 210 and the surrounding tissue. Based on the image analysis, for example via segmentation of the intra-procedure images, a density of the tumor 210 and the tissue of the margin 214 can be assessed. In addition, the segmentation can reveal the presence and size of blood vessels transiting the tumor 210 and margin 214. As is known the blood vessels act as heat sinks for applied energy, thus requiring more energy to achieve a successful ablation. The ablation application can utilize this assessment of the tumor 210 and margin 214 to determine appropriate power and duration settings for the generator 618. Still further, in instances where intraprocedural images are acquired to monitor the ablation, image analysis can be employed to alter the ablation parameters, for example ceasing ablation when a desired margin 214 is reached, or adjusting parameters, of power, duration, on/off cycles, etc. based on the progression of the ablation.

Yet a further aspect of the disclosure is directed to provision of guidance relating to how a change in position of the ablation catheter 600 with affect the ablation zone and a margin 214. Thus, using the intraprocedural images and the ablation application can depict in a user interface 200, 300 a projected change in shape and size of the ablation zone including the margin 214 around the tumor 210 that would result from either an advancement or a retraction of the ablation catheter 600. These may be displayed in a different color or as a translucent layer that allows the user to assess how a change in position might change the ablation and therewith the outcome for the patient.

Figure 8:
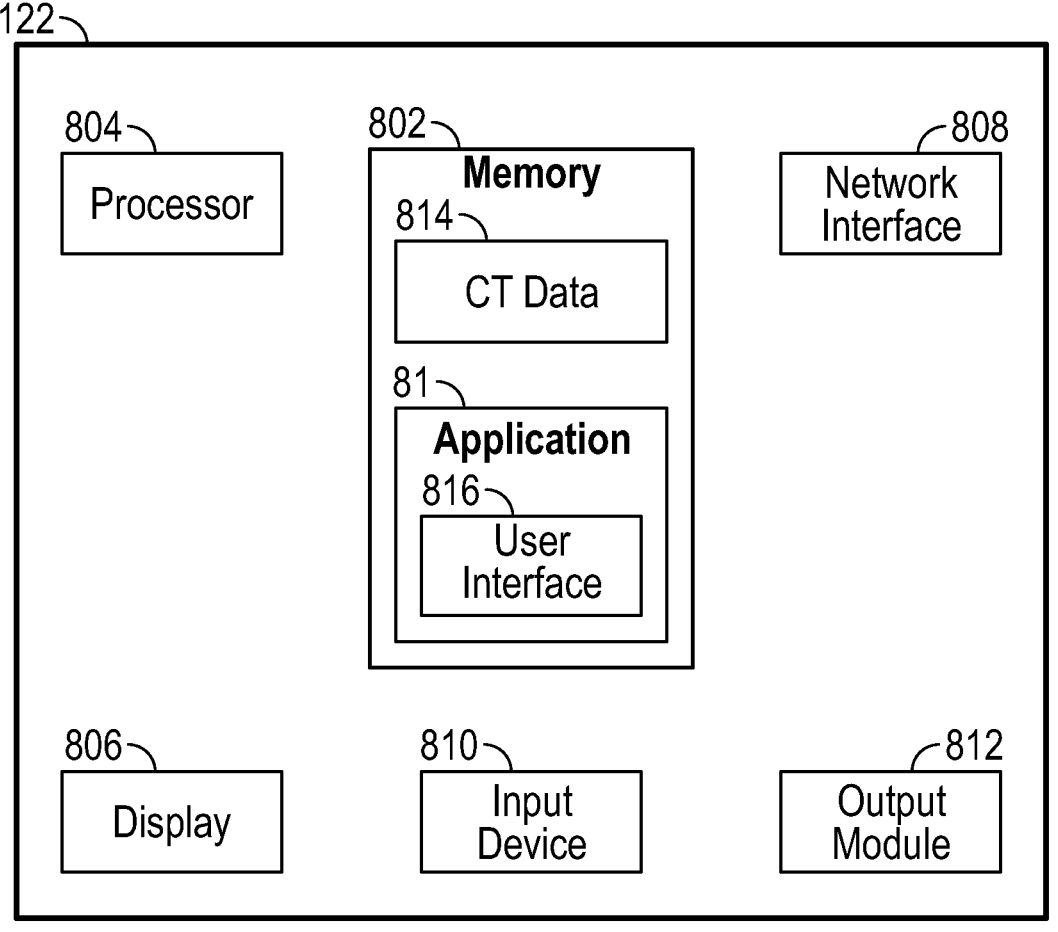
FIG. 8 is a schematic view of a computing device in accordance with the disclosure.

Turning now to FIG. 8, there is shown a system diagram of computing device 122 for enabling the methods and systems described herein. Computing device 122 may include memory 802, processor 804, display 806, network interface 808, input device 810, and/or output module 812.

Memory 802 includes any non-transitory computer-readable storage media for storing data and/or software that is executable by processor 804 and which controls the operation of workstation 80. In an embodiment, memory 802 may include one or more solid-state storage devices such as flash memory chips. Alternatively or in addition, to the one or more solid-state storage devices, memory 802 may include one or more mass storage devices connected to the processor 804 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 804. That is, computer readable storage media includes non-transitory, volatile, and non-volatile, removable, and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information, and which can be accessed by workstation 80.

Memory 802 may store application 81 and/or CT data 814. Application 81 may, when executed by processor 804, cause display 806 to present user interface 816. Network interface 208 may be configured to connect to a network such as a local area network (LAN) consisting of a wired network and/or a wireless network, a wide area network (WAN), a wireless mobile network, a Bluetooth network, and/or the internet. Input device 810 may be any device by means of which a user may interact with workstation 80, such as, for example, a mouse, keyboard, foot pedal, touch screen, and/or voice interface. Output module 812 may include any connectivity port or bus, such as, for example, parallel ports, serial ports, universal serial busses (USB), or any other similar connectivity port known to those skilled in the art.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A system for planning and navigation of a luminal network, comprising:

a computing device including a memory and a processor, the memory storing one or more applications that when executed by the processor execute the steps of:

receiving a computed tomography (CT) image data set;

generating a three-dimensional (3D) model;

causing display of the 3D model in a user-interface on a display operatively connected to the computing device;

receiving an indication of a location of a tumor in the CT image data set;

causing display of the location of the tumor in the 3D model;

receiving an indication of a margin around the tumor to achieve a desired therapy;

reducing the displayed 3D model to an airway generation level wherein the generation level is a selected number of generations beyond an identified point in an airway;

generating a pathway plan to the tumor for navigation of a catheter;

receiving a location of a sensor associated with a navigation catheter and registering the CT image data set with a luminal network of a patient;

causing display of the location of the sensor within the reduced 3D model that substantially corresponds to the location of the sensor within the luminal network of the patient;

causing the display of, following the pathway plan, the navigation of the navigation catheter to the tumor;

receiving an intraprocedural image data set;

updating a relative position of the tumor and the navigation catheter in the reduced 3D model based on the intraprocedural image data set;

displaying in the reduced 3D model the navigation catheter advanced into the tumor;

receiving a second intraprocedural image data set depicting the navigation catheter with respect to the tumor;

receiving an indication that an ablation catheter has been advanced through the navigation catheter; and initiating ablation of the tumor.

2. The system of claim 1, wherein the margin is automatically generated.

3. The system of claim 1, further comprising determining a location of an access point on a wall of the luminal network to access the tumor, wherein the tumor is located beyond an airway wall.

4. The system of claim 3, further comprising causing display of the access point on the user-interface at a location in the reduced 3D model.

5. The system of claim 1, further comprising receiving an indication that the ablation catheter is properly placed in the tumor.

6. The system of claim 5, further comprising causing display of a third intraprocedural image data set during the ablation of the tumor, wherein the intraprocedural image data set depicts a progression of the ablation.

7. The system of claim 6, wherein the first, second, and third intraprocedural image data sets are fluoroscopic images or cone beam CT images.

8. The system of claim 7, wherein the pathway plan is registered to the second or third intraprocedural image data sets.

9. The system of claim 8, further comprising causing;

display of at least a portion of the pathway plan, an access point, the tumor, or the margin on the second or third intraprocedural image data set;

display of an ablation zone on the third intraprocedural image data set; and receiving an instruction to adjust the ablation zone before initiating the ablation.

10. The system of claim 1, further comprising, receiving an indication of critical structures in the 3D model, wherein the critical structures are overlaid on the first or second intraprocedural image data set.

11. The system of claim 1, wherein during the first or second intraprocedural image data set acquisition certain frames of the image data set are skipped to reduce a radiation dose of the imaging.

12. The system of claim 1, further comprising receiving an indication of critical structures or key structures and a minimum distance to maintain from the critical structures or key structures.

13. A system for planning and navigation of a luminal network comprising:

a navigation catheter configured for insertion into a luminal network of a patient;

a sensor associated with the catheter for detecting a position of the navigation catheter within the luminal network of the patient;

an ablation catheter configured for receipt into the navigation catheter; and a computing device including a memory and a processor, the memory storing one or more applications that when executed by a processor:

causes display of a 3D model of the luminal network of a patient, the 3D model including airways and blood vessels of the luminal network, a pathway through the luminal network, a tumor including a margin, and where the tumor is located beyond an airway wall an access point, and a position of the catheter within the luminal network of the patient based on the detected position of the sensor;

reduces the 3D model to an airway generation level wherein the generation level is a selected number of generations beyond an identified point in an airway;

receives intraprocedural images; and overlays at least a portion of the reduced 3D model onto the intraprocedural images.

14. The system of claim 13, wherein the intraprocedural images are caused to display on a user-interface as the ablation catheter is inserted into the tumor.

15. The system of claim 14, wherein prior to insertion of the ablation catheter an ablation zone, determined prior to a therapy procedure, is displayed on the intraprocedural images and the ablation zone may be adjusted prior to initiation of the ablation.

16. A method comprising:

receiving a computed tomography (CT) image data set;

generating a three-dimensional (3D) model:

causing to display the 3D model in a user-interface on a display operatively connected to a computing device;

receiving an indication of a location of a tumor in the CT image data set;

causing display of the location of the tumor in the 3D model;

reducing the 3D model to an airway generation level wherein the generation level is a selected number of generations beyond an identified point in an airway;

receiving an indication of a margin around the tumor to achieve a desired therapy;

generating a pathway plan to the tumor for navigation of a catheter;

receiving a location of a sensor associated with a navigation catheter and registering the CT image data set with a luminal network of a patient;

causing to display the location of the sensor within the reduced 3D model that substantially corresponds to the location of the sensor within the luminal network of the patient;

causing to display, following the pathway plan, the navigation of the navigation catheter to tumor;

receiving an intraprocedural image data set;

updating a relative position of the tumor and the navigation catheter in the reduced 3D model based on the intraprocedural image data set;

causing to display in the reduced 3D model the navigation catheter advanced into the tumor;

receiving a second intraprocedural image data set depicting the navigation catheter with respect to the tumor;

receiving an indication that an ablation catheter has been advanced through the navigation catheter; and initiating ablation of the tumor.

17. The method of claim 16, further comprising determining a location of an access point on a wall of the luminal network to access the tumor, wherein the tumor is located beyond an airway wall.

18. The system of claim 1, wherein the identified point in the airway is the trachea.

19. The system of claim 13, wherein the identified point in the airway is the trachea.

20. The system of claim 15, wherein the identified point in the airway is the trachea.

* * * * *